United States Patent [19]

Manimaran et al.

[11] Patent Number: 5,162,576
[45] Date of Patent: Nov. 10, 1992

[54] RESOLUTION OF KETOPROFEN

[75] Inventors: Thanikavelu Manimaran; Alicia A. Potter, both of Baton Rouge, La.

[73] Assignee: Ethyl Corporation, Richmond, Va.

[21] Appl. No.: 684,809

[22] Filed: Apr. 15, 1991

[51] Int. Cl.⁵ .............................................. C07B 57/00
[52] U.S. Cl. .................................. 562/401; 546/136; 560/52; 562/460
[58] Field of Search .................... 562/401, 460; 560/52

[56] References Cited

U.S. PATENT DOCUMENTS

| | | | |
|---|---|---|---|
| 4,723,033 | 2/1988 | Erickson | 560/56 |
| 4,983,765 | 1/1991 | Lukas et al. | 562/401 |

FOREIGN PATENT DOCUMENTS 3824353  1/1990  Fed. Rep. of Germany .

OTHER PUBLICATIONS

Rendié, et al., *Chimia*, 29(4), 170–172, (1975).

*Primary Examiner*—Jose G. Dees
*Assistant Examiner*—Vera C. Clarke
*Attorney, Agent, or Firm*—Richard J. Hammond

[57] ABSTRACT

A method for resolving (±)-(α)-(3-benzoylphenyl) propionic acid is disclosed. The method comprises:
i) converting said propionic acid with (−)-cinchonidine in a solvent comprising a mixture of an aliphatic ester and an alkyl alcohol;
ii) separating teh diastereomeric salt from such conversion;
iii) purifying said separated diastereomeric salt by a single recrystallization; and
iv) isolating highly pure (+)-α-(3-benzoylphenyl) propionic acid without any further recrystallization.

14 Claims, No Drawings

RESOLUTION OF KETOPROFEN

FIELD OF INVENTION

The invention relates to a process for resolution of mixtures of enantiomeric arylpropionic acids and for obtaining one of the enantiomeric forms of the acids, in which the mixture is converted with a chiral base in an inert solvent to a diastereoisomeric salt and the desired acid enantiomer is separated therefrom.

BACKGROUND OF INVENTION

It has been firmly established that enantiomers with (S)-configuration of chiral derivatives of α-phenyl-propionic acid, as well as those of some other α-heteroaryl-propionic acids, possess predominant, if not exclusive, anti-inflammatory activity.

The resolution of the racemates has been successfully accomplished using both physical and chemical techniques.

Chromatographic separation has been carried out using a variety of substrates.

Coutts et. al. investigated enantiomeric mixtures of nonsteroidal anti-inflammatory drugs (NSAIDs). They discovered that these readily react with (+)- or (−)-amphetamine (AM) in the presence of 1,1'-carbonyldiimidazole. The resulting NSAID-AM diastereoisomeric amides are easily separated by gas chromatography (GC) or by a fused silica ME silicone capillary column. See *Development of Drugs in Modern Medicine*, 232–6, Edited by Gorrod et. al., Herwood, Chichester, U.K. (1986).

Profen derivatives and some other acidic compounds were resolved by using HPLC with an ovomucoid-conjugated column. The retention of acidic compounds was markedly reduced by the addition of sodium octane sulfonate, while that of amines was reduced by a cationic ion-pairing agent. The ovomucoid-conjugated column exhibited the best chiral recognition ability when the protein molecule was in a state as close as possible to its native form. See Miwa et. al., *J. Chromatog.*, 408, 316–22 (1987).

In Okamota et. al., *Chirality*, 1(3) 239–42 (1989), the direct optical resolution of anti-inflammatory drugs such as ibuprofen, ketoprofen, and flurbiprofen acid was attempted by HPLC using tris(3,5-dimethylphenylcarbamate)s of cellulose and amylose as chiral stationary phases. Although ibuprofen was not sufficiently resolved, the other three 2-arylpropionic acids were completely resolved by the amylose derivative. Ibuprofen was resolved as the anilide derivative.

Rendic et. al., *Chimia*, 29(4) 170–172 (1975) describes the resolution of ketoprofen by (R)-α-phenylethylamine. The products were separated by column chromatography on silica.

However, chromatographic separations, while useful as an analytical tool, are not typically capable of producing large amounts of materials for commercial utility.

Chemical separation is described, for example, in U.S. Pat. No. 4,209,638. A diastereomeric mixture of a salt of 2-arylpropionic acid and an inert liquid organic diluent was heated to at least 80° C. So much salt was used that part remained undissolved in the diluent. Heating was continued until part of one of the optical isomers of the acid component was resolved to its enantiomer by salt formation. The acid component was then separated. The process requires, in addition to a considerable volume of solvent, relatively high temperatures and, in some cases, the application of pressure also being necessary during operation. Nevertheless, the purity of the obtained product leaves something to be desired. The process is both space-consuming and time-consuming, and therefore runs into difficulties on the industrial scale.

The object of the present invention is to provide an efficient and practical process for the separation of a racemic mixture of ketoprofen [(±)-α-(3-benzoylphenyl)propionic acid] into its individual enantiomeric forms, particularly the S(+) form.

SUMMARY OF INVENTION

In the process of the present invention, it has been discovered that the ketoprofen-cinchonidine salt forms from a solution of an aliphatic ester and alkyl alcohol. The diastereomeric forms of the salt are readily separated and further purified in a single recrystallization. The separated salt is easily hydrolyzed to afford the highly pure (S)-(+)-ketoprofen without the need for any further recrystallization.

DESCRIPTION OF THE PREFERRED EMBODIMENTS

In the process of the present invention, the term aliphatic ester means an ester of the formula $RC(O)OR_1$, where R and $R_1$ are the same or different and are $C_1$ to $C_{12}$ linear or branched alkyl, for example, methyl, ethyl, propyl, isopropyl, butyl, pentyl, neopentyl, hexyl, nonyl, dodecyl and the like. Preferably, R and $R_1$ are the same or different and are $C_1$ to $C_6$ linear or branched alkyl. Most preferred are the $C_1$ to $C_6$ linear or branched alkyl esters of acetic acid. A particularly preferred aliphatic ester is ethyl acetate.

Alkyl alcohol means the $C_1$ to $C_{12}$ linear or branched alkyl alcohols such as methanol, ethanol, n-propanol, n-butanol, n-hexanol, 2-ethylhexanol, nonan-1-ol and the like. Preferably, the alkyl group is a $C_1$ to $C_6$ linear or branched alkyl. Particularly preferred is methanol.

In carrying out the process of the present invention, racemic ketoprofen, obtained commercially, is dissolved in a solvent mixture of an aliphatic ester and alkyl alcohol. The solution is heated to from about 30° C. to about 70° C., preferably about 50°–60° C., and cinchonidine is added. Typically for best results, an equal equivalent weight of cinchonidine to ketoprofen is used in this reaction. However, it should be understood that more than an equivalent weight of cinchonidine can be used, facilitating the complete reaction of the ketoprofen.

In some cases, it has been found that a vigorously stirred first solution of racemic ketoprofen and cinchonidine at 30°–20° C. to which methanol is next added favors the completeness of the reaction. However, such two-step sequence of solvent addition is not required to produce the highly pure diastereomer for the process of the present invention.

The solvent system ratios are critical to achieving the highly pure material isolated from the present process. Thus, the (volumetric) amount of aliphatic ester should be from about 2 to about 20 times the amount of alkyl alcohol, preferably about 15 times, most preferably about 7 to about 12 times such amount.

The ratio of salt to solvent is in the range of 1:0.2 to 1:100, preferably 1:0.6 to 1:15 (w/v).

At the conclusion of the reaction, usually about 15 to about 60 minutes, the diastereomeric salt is separated from the optionally cooled reaction solution. A single recrystallization (from ethyl acetate/methanol) produces a sufficiently pure salt for further (hydrolysis) treatment. While further recrystallizations are possible, they are not needed since the optical purity of the diasteromeric salt is very high, typically over 95%.

The diastereomeric salt is cleaved with dilute hydrochloric and the S(+)ketoprofen separated.

The process of the present invention is set forth below in more detail in the form of specific non-limiting and illustrative examples.

EXAMPLES

General

Melting point was determined on a Mel-Temp II apparatus and is uncorrected. NMR spectra were recorded on a GE QE 300-MHz spectrometer. Carbon and proton shifts were reported in parts per million relative to tetramethylsilane. Infrared spectra were obtained on a Nicolet 20SXB FTIR spectrometer. Optical rotations were taken with a Perkin Elmer 241 Polarimeter and refer to $CH_2Cl_2$ 10% solution, at 20° C. and 589 nm, unless otherwise noted. HPLC analyses were performed on an HP 1090 instrument according to the Chiral AGP 100-4 method.

GC analyses were carried out on an HP 5890 instrument equipped with a 15-meter DB-1 megabore column (0.53 mm i.d.; temperature program: 100°–250° C. at 10° /min.) and a flame ionization detector. The carrier gas was helium (flow-rate @5 mL/min.) with an inlet pressure of 2 p.s.i. All samples were derivatized with (S)-α-methylbenzylamine (MBA) prior to injection. Results are reported as area percent.

Formation of the (S)-(−)-Ketoprofen-cinchonidine salt

Cinchonidine (155 g; 0.53 mol) was added to a solution of 115g (0.59 mol) of racemic ketoprofen and 2.8 L of ethyl acetate under vigorous stirring at 50°–60° C. The mixture was diluted with 280 mL of methanol, cooled to 35° C., then seeded with 98% enantiomerically pure S-salt to induce crystallization. After stirring at room temperature for 16 h and 0° C. for 5–6 h, the precipitated diastereomeric salt was filtered under vacuum, washed three times with ethyl acetate and three times with ether, and then dried under vacuum for 16 h [Yield: 127 g (or 44%); enantiomeric purity: 86% S]. One recrystallization from 1.7 L of ethyl acetate/methanol (10:1) afforded 88 g (31% yield) salt of 97% enantiomerically pure S-ketoprofen.

This salt was combined with two other batches of salt, which were prepared under the same conditions to liberate S-ketoprofen.

Isolation of (S)-(+)-2-(3-Benzoylphenyl)propionic acid

A 215 g sample of the salt was dissolved in 1400 mL of 10% aqueous HCl and the resulting mixture was extracted with four 500-mL portions of ether. The combined ether extracts were washed with an additional 500 mL of aqueous HCl and the layers were separated. The organic layer was dried with $MgSO_4$, and then the solvent was removed in vacuo. The crude product was rinsed with 500 mL of petroleum ether, filtered, pulverized, and dried under vacuum at room temperature for 16 h to yield 92 g (or 92%) of S-ketoprofen (enantiomeric purity=97%). mp 73.2–74.7° C.; [α]= +54.3°; $^1$H NMR:7.82–7.40 (9 H, m, aromatic H), 3.82 (1 H, q, CHCH$_3$), 1.53 (3 H, d, CHCH$_3$); $^{13}$C NMR (CDCl$_3$):18 (CH$_3$), 45 (CH)(, 128–132 (aromatic CH), 137–140 (aromatic CR), 179 (RCOOH), 196(RCOR); IR(KBr) cm$^{-1}$: 3100–3600 (OH), 3160 (aromatic CH), 2850–2950 (aliphatic CH), 1720 (COOH), 1650 (C=O), 1280 (COOH).

TABLE I

Determination of Optimal Conditions for the Resolution of Ketoprofen[a]

| Example | Derivatizing Agent | Equivalence Used | Solvent(s) | No. of Recrystallizations | % Yield of Salt[b] | % S (GC Area %) | % S (HPLC Area %) | Rotation[c] |
|---|---|---|---|---|---|---|---|---|
| 1 | MBA | 1 | THF/Hexanes[d] | 2 | 25 | nd | nd | +11(MeOH) |
| 2 | DHA | 1 | THF/Hexanes[d] | 2 | 10 | nd | nd | +18(MeOH) |
| 3 | CD[e] | 1 | Acetone/Methanol/Hexanes[f] | 2 | 11 | nd | 99 | +39(MeOH) |
| 4[g] | CD[e] | 1 | Acetone/Methanol | 0 | 24 | 91 | 93 | +48(CH$_2$Cl$_2$) +41(MeOH) |
| 5[g] | MBA | ½ | 2-Propanol | 2 | 20 | nd | nd | +13(MeOH) |
| 6[h] | CD[e] | ½ | Acetone | 5 | 08 | 97 | >99 | nd |
| 7 | CD[e] | ½ | Ethyl acetate | 1 | 74 | nd | 50 | nd |
| 8 | CD[e] | 1 | Ethyl acetate | 1 | 48 | nd | 54 | nd |
| 9 | CD[e] | ½ | Ethyl acetate/Hexanes | 0 | 73 | nd | 52 | nd |
| 10 | CD[e] | 1 | Ethyl acetate/Methanol | 1 | 18 | nd | 97 | nd |
| 11 | CD[i] | ½ | Acetone/Octane | 4 | 39 | 97 | >99 | nd |
| 12 | CD[i] | 1 | Acetone/Octane | 4 | 28 | 97(98)[j] | 98 | +55(CH$_2$Cl$_2$) |
| 13 | CD[i] | 1 | Ethyl acetate/Methanol | 1 | 31 | .(97) | 97 | +54(CH$_2$Cl$_2$) |
| 14 | CD[k] | 1 | Acetone/Octane | 5 | 21 | 98(99) | >99 | +54(CH$_2$Cl$_2$) |
| 15[f] | MBA | nd | Ethyl acetate | 0 | nd | nd | 56 | nd |

TABLE I-continued

Determination of Optimal Conditions for the Resolution of Ketoprofen[a]

| Example | Derivatizing Agent | Equivalence Used | Solvent(s) | No. of Recrystallizations | % Yield of Salt[b] | % S (GC Area %) | % S (HPLC Area %) | Rotation[c] |
|---|---|---|---|---|---|---|---|---|
| 16 | CD[e] | ½ | 2-Propanol/Hexanes | 0 | 80 | 53 | nd | nd |
| 17[h] | CD[e] | ½ | 2-Propanol | 3 | 5 | 93 | nd | nd |

[a]Reactions were carried out between room temperature and the respective boiling point of the solvent. A mixture of racemic ketoprofen and the derivatizing agent was dissolved in the appropriate volume of solvent and slowly cooled to room temperature to allow crystallization. The salt was separated from the solvent and recrystallized. S-Ketoprofen was isolated by acidifying with HCl and extracting with ether or ethyl acetate.
[b]Yields were calculated as percentage of total diastereomeric salt, assuming that the derivatizing agent is the limiting reagent.
[c]Specific rotations refer to a 10% solution in the given solvent.
[d]Second recrystallization of salt was from 2-propanol and hexanes.
[e]Aldrich cinchonidine (90% pure) was used.
[f]Salt was recrystallized from 2-propanol and hexanes.
[g]Experiment was performed at room temperature.
[h]One equivalent of triethylamine was added.
[i]Fluka cinchonidine (98% pure) was used.
[j]Parenthetical data is for sample that was prepared with purified MBA.
[k]Recrystallized cinchonidine (>99% pure) was used.
MBA = (S)-(−)-α-Methylbenzylamine.
DHA = Dehydroabiethylamine.
CD = (−)-Cinchonidine.

We claim:

1. A method for resolving (±)-(α)-(3-benzoylphenyl)-propionic acid comprising:
   (i) converting said propionic acid with (−)-cinchonidine in a solvent comprising a mixture of an aliphatic ester and an alkyl alcohol, said aliphatic ester being from about 2 to about 20 times in excess of said alkyl alcohol;
   (ii) separating the diastereomeric salt from such conversion;
   (iii) purifying said separated diastereomeric salt by a single recrystallization; and
   (iv) isolating highly pure (+)-(α)-(3-benzoylphenyl)-propionic acid without any further recrystallization.

2. The method according to claim 1 wherein said aliphatic ester is ethyl acetate.

3. The method according to claim 1 wherein said alkyl alcohol is selected from the group consisting of methyl alcohol, ethyl alcohol, n-propyl alcohol and i-propyl alcohol.

4. The method according to claim 3 wherein said alcohol is methyl alcohol.

5. A method for resolving (±)-(α)-(3-benzoylphenyl)-propionic acid comprising:
   (i) converting said propionic acid with (−)-cinchonidine in a solvent at 30°-70° C., comprising a mixture of an aliphatic ester and an alkyl alcohol, said aliphatic ester being from about 2 to about 20 times in excess of said alkyl alcohol;
   (ii) separating the diastereomeric salt from such conversion;
   (iii) purifying said separated diastereomeric salt by a single recrystallization; and
   (iv) isolating highly pure (+)-(α)-(3-benzoylphenyl)-propionic acid without any further recrystallization.

6. The method according to claim 5 wherein said aliphatic ester is ethyl acetate.

7. The method according to claim 5 wherein said alkyl alcohol is selected from the group consisting of methyl alcohol, ethyl alcohol, n-propyl alcohol and i-propyl alcohol.

8. The method according to claim 7 wherein said alcohol is methyl alcohol.

9. A method for resolving (+)-(α)-)3-benzoylphenyl)-propionic acid comprising:
   (i) converting said propionic acid with (−)-cinchonidine by admixing said propionic acid and said cinchonidine with an aliphatic ester solvent;
   (ii) adding to said admixture an alkyl alcohol, said aliphatic ester being about 2 to about 20 times in excess of said alkyl alcohol;
   (iii) repeating a diastereomeric salt from said admixture of step ii,
   (iv) purifying said separated diastereomeric salt by a single recrystallization; and
   (v) isolating highly pure (±)-(α)-(3-benzoylphenyl)-propionic acid without any further recrystallization.

10. The method according to claim 9 wherein said aliphatic ester is ethyl acetate.

11. The method according to claim 9 wherein said alkyl alcohol is selected from the group consisting of methyl alcohol, ethyl alcohol, n-propyl alcohol and i-propyl alcohol.

12. A method for resolving (+)-(α)-(3-benzoylphenyl)-propionic acid comprising:
   i. converting said propionic acid with (−)-cinchonidine by admixing said propionic acid and said cinchonidine with an aliphatic ester solvent at 30°-70° C;
   ii. adding to said admixture an alkyl alcohol, said aliphatic ester being about 2 to about 20 times in excess of said alkyl alcohol;
   iii. repeating a diastereomeric salt from said admixture of step ii;
   iv. purifying said separated diastereomeric salt by a single recrystallization; and
   v. isolating highly pure (±)-(α)-(3-benzoylphenyl)-propionic acid without any further recrystallization.

13. The method according to claim 12 wherein said aliphatic ester is ethyl acetate.

14. The method according to claim 12 wherein said alkyl alcohol is selected from the group consisting of methyl alcohol, ethyl alcohol, n-propyl alcohol and i-propyl alcohol.

* * * * *